United States Patent [19]
Dodey et al.

[11] Patent Number: 5,968,951
[45] Date of Patent: Oct. 19, 1999

[54] BENZENESULFONAMIDE DERIVATIVES AS BRADYKININ ANTAGONISTS

[75] Inventors: Pierre Dodey, Fontaine-Lès-Dijon; Didier Pruneau, Pasques; Jean-Luc Paquet, Dijon; Michel Bondoux, Fontaine-lès-Dijon; Patrick Houziaux, Bazemont; Martine Barth, Montfort-l'Amaury; Khan Ou, Hauteville-lès-Dijon, all of France

[73] Assignee: Fournier Industrie et Sante, Paris, France

[21] Appl. No.: 08/776,544

[22] PCT Filed: Jun. 5, 1996

[86] PCT No.: PCT/FR96/00845

§ 371 Date: Jan. 31, 1997

§ 102(e) Date: Jan. 31, 1997

[87] PCT Pub. No.: WO96/40639

PCT Pub. Date: Dec. 19, 1996

[30] Foreign Application Priority Data

Jun. 7, 1995 [FR] France ................... 95 06 703

[51] Int. Cl.[6] .................. A61K 31/47; C07D 215/36
[52] U.S. Cl. ................... 514/311; 514/314; 546/172
[58] Field of Search ............... 546/172; 574/311, 574/314

[56] References Cited

U.S. PATENT DOCUMENTS 5,059,610 10/1991 Huang ........................ 514/314
5,212,182 5/1993 Musser et al. ............... 514/314
5,563,162 10/1996 Oku ........................... 514/311

FOREIGN PATENT DOCUMENTS 0 261 539 3/1988 European Pat. Off. .
0 596 406 5/1994 European Pat. Off. .
0 622 361 11/1994 European Pat. Off. .
2533821 2/1977 Germany .

OTHER PUBLICATIONS

Stewart JM. Biopolymers. 37, 143–155, 1995.
Stewart JM. Agents and Actions Suppl. 38(I), 546–550, 1992.

*Primary Examiner*—Evelyn Mei Huang
*Attorney, Agent, or Firm*—Evenson, McKeown, Edwards, Lenahan, PLLC

[57] ABSTRACT

The present invention relates to novel compounds of the formula (I)

in which:

X is a halogen atom, $R_1$ and $R_2$, which are identical or different, are each —H or —A—B—$R_3$, A is a linear or branched $C_1$–$C_{12}$-alkylene chain, B is a single bond, a divalent phenylene group or a divalent indolyl group of the structure $R_3$ is —H, —OH, —$NR_4R_5$ or —$COR_6$, $R_6$ is —OH, —$OCH_3$, —$OC_2H_5$ or —$NR_4R_5$, $R_4$ and $R_5$, which are identical or different, are each H, a $C_1$–$C_4$-alkyl group, —$(CH_2)_n$—OH, —$(CH_2)_n$—N$(CH_3)_2$ or —CO—$CH_3$, and n is an integer with a value of 2, 3 or 4; and their addition salts. It further relates to their preparation and to their use in therapeutics, especially for the treatment of pathological conditions involving bradykinin.

12 Claims, No Drawings

BENZENESULFONAMIDE DERIVATIVES AS BRADYKININ ANTAGONISTS

This application is the national phase of PCT/FR96/00845, filed Jun. 6, 1996, published as WO 96/40639 on Dec. 19, 1996.

FIELD OF THE INVENTION

The present invention relates to novel benzenesulfonamide compounds, to the process for their preparation and to their use in therapeutics.

These novel compounds have especially an antagonistic action towards bradykinin and are useful in therapeutics, particularly for the treatment of pain and inflammation and especially in the treatment of asthma and allergic rhinitis.

PRIOR ART

It is known that one of the possible ways of treating certain pathological conditions of a painful and/or inflammatory nature (such as asthma, rhinitis, septic shock, toothache, etc.) is to antagonize the action of certain hormones such as bradykinin or kallidin. These peptide hormones are in fact involved in a large number of physiological processes, some of which are closely associated with these pathological conditions.

Although no products possessing this mode of action have yet been marketed, numerous studies have been undertaken to create compounds capable of being bradykinin receptor antagonists. Bradykinin is a peptide hormone consisting of 9 amino acids (Arg-Pro-Pro-Gly-Phe-Ser-Pro-Phe-Arg) and kallidin is a peptide hormone (Lys-Arg-Pro-Pro-Gly-Phe-Ser-Pro-Phe-Arg) which has an additional amino acid (Lys) compared with bradykinin. Earlier studies are known to have produced peptides which react with the bradykinin receptors: some, such as bradycor (CP.0127 from Cortech), icatibant (HOE 140 from Hoechst) ["bradycor" and "icatibant" are international non-proprietary names (INN)] or NPC 17761 (from Scios-Nova), have an inhibitory action on the binding of bradykinin to the bradykinin $B_2$ receptor. More recently, non-peptide compounds have been proposed as bradykinin antagonists in respect of binding to the bradykinin $B_2$ receptor, especially in EP-A-0596406 and EP-A-0622361. It is also known that certain compounds structurally related to those described in the two patent applications cited above have already been described as possibly having antithrombotic properties, especially in DE-A-3617183 and EP-A-0261539.

OBJECT OF THE INVENTION

There is a need for ways to reduce or eliminate pain and inflammation in mammals and particularly in man.

To meet this need, a novel technical solution has been sought which is effective on the one hand in the treatment of pain, irrespective of its origin, especially that associated with inflammatory phenomena, and on the other hand in the treatment of inflammation.

According to the invention, it is proposed to provide a novel technical solution which uses competitive binding, at the bradykinin $B_2$ receptor, between (i) bradykinin and related or analogous hormones, and (ii) an antagonistic substance, and utilizes benzenesulfonamide compounds which are structurally different from the known products mentioned above and which limit or substantially inhibit the binding of bradykinin and analogous hormones to said bradykinin $B_2$ receptor.

In accordance with this novel technical solution, it is proposed according to a first feature of the invention to provide benzenesulfonamide compounds as novel industrial products, according to a second feature of the invention to provide a process for the preparation of these compounds, and according to a third feature of the invention to provide the use of these compounds, especially in therapeutics, as analgesic and/or anti-inflammatory active ingredients.

SUBJECT OF THE INVENTION

In accordance with the novel technical solution of the invention, a benzenesulfonamide compound is recommended as a novel industrial product, said compound being characterized in that it is selected from the group consisting of:

(i) the compounds of the formula

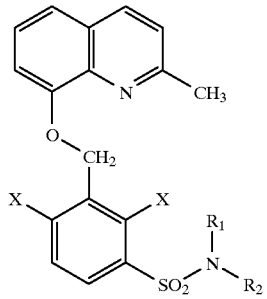

(I)

in which:

X is a halogen atom, $R_1$ and $R_2$, which are identical or different, are each a hydrogen atom or a group —A—B—$R_3$, A is a linear or branched $C_1$–$C_{12}$-alkylene chain, B is
- a single bond,
- a phenylene group of the structure

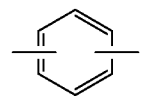

relative to which the substituents A and $R_3$ are in the ortho, meta or para position, or
- a divalent indolyl group of the structure

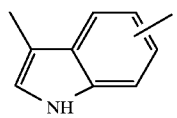

$R_3$ is —H, —OH, —$NR_4R_5$ or —$COR_6$, $R_6$ is a group —OH, —$OCH_3$, —$OC_2H_5$ or —$NR_4R_5$, $R_4$ and $R_5$, which are identical or different, are each a hydrogen atom, a $C_1$–$C_4$-alkyl group with a linear or branched hydrocarbon chain, a group —$(CH_2)_n$—OH, a group —$(CH_2)_n$—$N(CH_3)_2$ or a group —CO—$CH_3$, and n is an integer with a value of 2, 3 or 4; and (ii) their addition salts.

The benzenesulfonamides according to the invention can be prepared by a method known per se by the application of conventional reaction mechanisms. Nevertheless, the process recommended according to the invention for the preparation of the benzenesulfonamide compounds of formula I and their addition salts is characterized in that it comprises a condensation reaction of 8-hydroxy-2-methylquinoline in the form of a phenate of the formula (VIII)

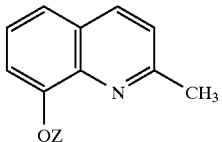

in which Z is an alkali metal atom, with a halogenated toluenesulfonamide of the formula (IX)

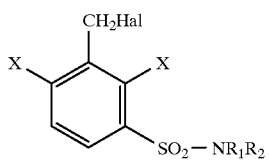

in which Hal is a halogen atom and X, $R_1$ and $R_2$ are defined as indicated above, the functional groups (especially alcohol —OH, primary amine —$NH_2$ and secondary amine —NH—) which may be contained in $R_1$ and/or $R_2$ and may take part in the reaction VIII+IX→I being protected.

The use of a substance selected from the compounds of formula I and their non-toxic addition salts is also recommended for obtaining a drug intended for use in therapeutics to combat pathological conditions involving bradykinin or its analogs, in particular to combat pain, and especially in the treatment or prevention of pathological conditions associated with inflammatory or painful states.

DETAILED DESCRIPTION OF THE INVENTION

In general formula I of the compounds of the invention, the halogen atom is the fluorine, chlorine, bromine or iodine atom, the preferred halogen being the chlorine atom.

$C_1$–$C_4$-Alkyl group is understood as meaning the methyl, ethyl, propyl, 1-methylethyl, butyl, 1,1-dimethylethyl, 1-methylpropyl or 2-methylpropyl group.

"Addition salts" are understood as meaning the acid addition salts obtained by reacting a compound of formula I with a mineral acid or an organic acid. The preferred mineral acids for salifying a basic compound of formula I are hydrochloric, hydrobromic, phosphoric and sulfuric acids. The preferred organic acids for salifying a basic compound of formula I are methanesulfonic, maleic, fumaric, oxalic, citric and trifluoroacetic acids.

For the sake of convenience, the benzenesulfonamide compounds which act as antagonists are arbitrarily mentioned as being either bradykinin antagonists or bradykinin $B_2$ receptor antagonists.

From the point of view of pharmacological activity, the preferred compounds of formula I according to the invention are those belonging to the group consisting of the compounds of the formula

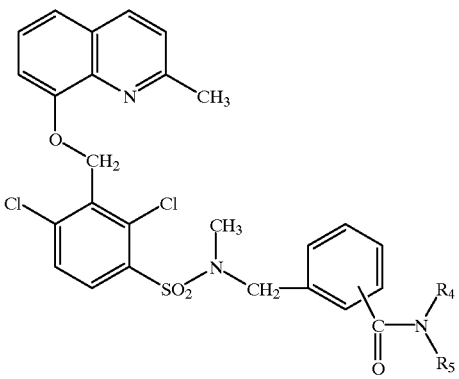

in which the amide group can be in the ortho, meta or para position and $R_4$ and $R_5$, which are identical or different, are each:
a hydrogen atom,
a linear or branched $C_1$–$C_4$-alkyl group,
a group —$(CH_2)_n$—OH, or
a group —$(CH_2)_n$—$N(CH_3)_2$,
where n is an integer with a value of 2, 3 or 4; and their non-toxic acid addition salts.

The general process for the preparation of the benzenesulfonamide compounds according to reaction (1):

VIII+IX→I  (1)

is carried out in an aprotic solvent [such as, in particular, dimethylformamide (DMF) or tetrahydrofuran (THF)], at a temperature between 0 and 50° C., the alkali metal Z being Li, K or, preferably, Na.

The phenate VIII can be prepared in situ for carrying out the reaction VIII+IX→I. In this reaction it can be advantageous for the electronegativity of the halogen atom Hal of the compound IX to be less than or equal to that of the halogen atom X; from a practical point of view, if X is Cl then Hal will advantageously be Br.

Finally, the reaction VIII+IX→I entails the protection of the reactive functional groups which may be present in the groups $R_1$ and/or $R_2$. These reactive functional groups include the groups —OH, —$NH_2$ and —NH—, which contain a reactive hydrogen atom capable of disturbing the course of the desired reaction (1).

By way of illustration, practical modalities of the reaction VIII+IX→I are given in Preparation III below.

All the compounds of formula I are prepared in accordance with the following reaction scheme:
(α) a compound of the formula (V)

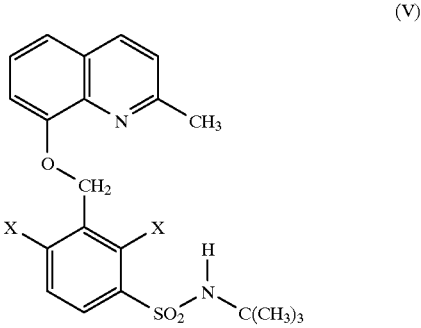

[which is a compound of formula I in which $R_2$ is H and $R_1$ is $C(CH_3)_3$] is synthesized according to reaction (1) given above, (β) if necessary, the compound of formula V is treated in order to replace the group $R_2$=H with a group $R_2$ other than H to give a compound of the formula (Va)

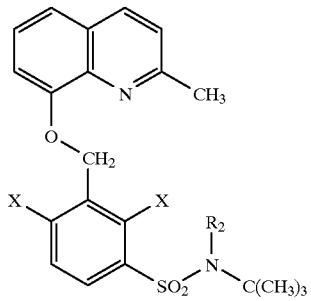

(γ) if necessary, the resulting compound of formula Va is treated in order to replace the group $R_1$=C(CH$_3$)$_3$ with the hydrogen atom to give a compound of the formula (Vb)

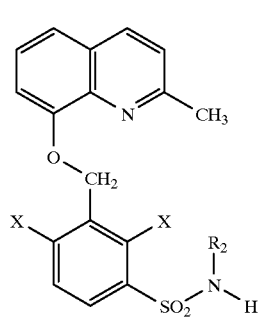

then
(δ) if necessary, the resulting compound of formula Vb is treated in order to replace the group $R_1$=H with a group $R_1$ other than H to give a compound of formula I in which both $R_1$ and $R_2$ are other than H,
and
(ε) if necessary, the acid addition salt of the free base resulting from stage (β). (γ) or (δ) is obtained [by reacting said free base with the acid chosen for salification].

Stages (β), (γ) and (δ) entail the protection and then deprotection of any reactive group which may be contained in $R_1$ and/or $R_2$.

From a practical point of view, the reaction scheme given above will be applied in a variant selected from the group consisting of variant A, which comprises the steps consisting in:
1) reacting a compound of the formula (II)

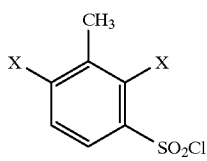

in which X is a halogen atom, with excess tert-butylatine (alternative nomenclature: 1,1-dimethylethanamine), in a solvent such as, for example, dichloromethane, at room temperature, for 1 to 3 hours, to give a compound of the formula (III)

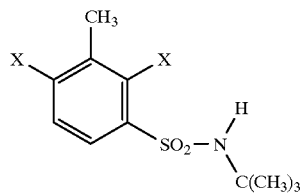

in which X is a halogen atom,
2) halogenating the compound III obtained above with an N-halogenosuccinimide (preferably N-bromosuccinimide), in a halogenated solvent, especially carbon tetrachloride, and preferably in the presence of a free radical initiator, especially AIBN [alternative nomenclature: 2,2'-azobis(2-methylpropionitrile) or 2,2'-azobis-(isobutyronitrile)], and/or in the presence of ultraviolet radiation, for 2 to 24 hours, at a temperature between 30° C. and 100° C., to give a compound of the formula (IV)

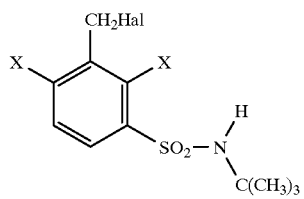

in which X and Hal are each a halogen atom,
3) condensing the resulting compound IV with 8-hydroxy-2-methylquinoline, the latter first being reacted with sodium hydride, in the presence of a solvent (especially DMF), at a temperature between 0° C. and 50° C., to give the compound of the formula (V)

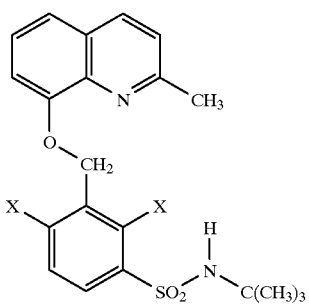

in which X is a halogen atom, and
4) reacting the resulting compound of formula V with sodium hydride, in an anhydrous organic solvent (especially DMF), at a temperature between 0° C. and 30° C., and then reacting the resulting sodium derivative with a compound of the formula Y—$R_2$, in which:
Y is a halogen atom (especially an iodine atom, a bromine atom or a chlorine atom), a methanesulfonyl group or a toluenesulfonyl group, and
$R_2$ is a $C_1$–$C_{12}$-alkyl group or an arylalkyl group, these two groups optionally being substituted by one or more protected functional groups so as not to react with the sodium sulfonamide, to give a compound of the formula (I)

[Chemical structure: 8-hydroxyquinoline with 2-methyl substituent, linked via O-CH2 to a benzene ring with two X substituents and an SO2-N(R1)(R2) group]

in which:
X is a halogen atom,
R$_1$ is the 1,1-dimethylethyl group, and
R$_2$ is as defined above; and variant B, which comprises the steps consisting in:
1) treating a compound of formula I obtained in step 4) of variant A, in which R$_2$ is the methyl group or the phenylmethyl group and R$_1$ is the 1,1-dimethylethyl group, with an excess of acid (especially trifluoroacetic acid), in the presence of a cation scavenger (especially anisole), at a temperature between 20° C. and 60° C., for 4 to 24 hours, to give a compound of the formula (I)

[Chemical structure similar to above]

in which:
X is a halogen atom,
R$_1$ is a methyl group or a phenylmethyl group, and
R$_2$ is a hydrogen atom, 2) treating the compound of formula I obtained in stage B 1) above with a compound of the formula YR$_2$, under conditions identical to those recommended in stage 4) of variant A, to give a compound of the formula (I)

[Chemical structure similar to above]

in which:
X is a halogen atom,

R$_1$ is a methyl group or a phenylmethyl group, and
R$_2$ is a C$_1$–C$_{12}$-alkyl group or an arylalkyl group, these two groups optionally being substituted by protected functional groups so as not to react with the sodium sulfonamide group, 3) if necessary, deprotecting the functional group or groups carried by the group R$_2$ of the compound of formula I obtained in one of stages A 4) or B 2) above (especially by hydrolysis of an ester or deprotection of an amine) to give a compound of formula I in which the group R$_2$ carries a free functional group, for example a free carboxylic acid group or primary amine group, 4) if necessary, reacting the functional group freed in the previous stage to give a derivative, for example an amide by reacting a carboxylic acid group with a compound carrying a primary or secondary amine group, and 5) if necessary, obtaining an addition salt of a compound of formula I initially obtained in the form of the free base, by reacting said free base with the acid chosen for salification.

Protected functional group is understood here as meaning especially:
a group NH or NH$_2$ protected by one or two amino-protecting groups,
an ester group,
an N-monosubstituted or N-disubstituted carboxamide group, or
a group OH protected by a hydroxyl-protecting group.

The amino-protecting groups suitable here are those which are customarily employed in the field of peptide synthesis, in particular alkoxycarbonyl groups and especially the group Boc (t-butoxycarbonyl). Examples of the hydroxyl-protecting groups are silyl groups (especially trimethylsilyl or dimethyl-t-butylsilyl) or groups of the benzyl type.

To illustrate step 3) of variant B, the procedure is as follows: A compound of the formula (VI)

[Chemical structure: 8-hydroxyquinoline derivative linked via O-CH2 to benzene ring with two X substituents and SO2-N(R1)-CH2-phenyl-COOR' group]

in which:
X is a halogen atom,
R$_1$ is a C$_1$–C$_4$-alkyl or arylalkyl group, and
R' is a methyl or ethyl group, is reacted with sodium hydroxide solution, in the presence of a solvent such as, for example, methanol, at a temperature between 40° C. and 80° C., for 0.5 to 5 hours, to give a compound of formula VI in which X and R$_1$ are as defined above and R' is a hydrogen atom.

To illustrate step 4) of variant B, the procedure is as follows: A resulting compound of formula VI in which R' is a hydrogen atom is reacted with an amine of the formula H—NR$_4$R$_5$, in which:
R$_4$ and R$_5$, which are identical or different, are each a hydrogen atom, a C$_1$–C$_4$-alkyl group (linear or branched), a group (CH$_2$)$_n$—OH or a group (CH$_2$)$_n$N(CH$_3$)$_2$, where n is an integer with a value of 2, 3 or 4, in a solvent such as, for example, dichloromethane, in the presence of coupling agents such as, for example, N,N'-dicyclohexylcarbodiimide and 1-hydroxybenzo-triazole, at a temperature close to room temperature, for 10 to 48 hours, to give a compound of the formula (VII)

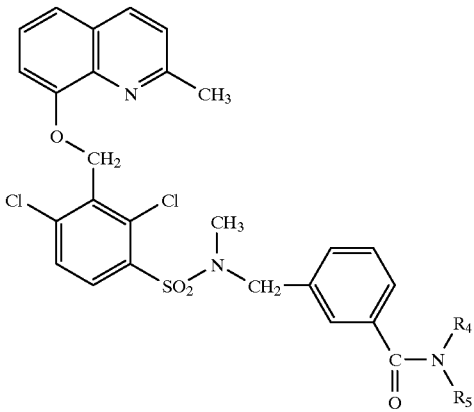

in which X, $R_4$ and $R_5$ are as defined above.

The compound of formula IV in which X is a chlorine atom and Hal is the bromine atom is novel and forms one of the subjects of the invention.

The invention will be understood more clearly from the following Preparatory Examples and the results of pharmacological tests obtained with some of the compounds according to the invention. The nomenclature used in these Examples is that which is recommended in Chemical Abstracts.

In the experimental section the "Preparations" relate to the intermediates and the "Examples" relate to the products according to the invention.

Some of the compounds are characterized by the spectral data obtained by nuclear magnetic resonance (NMR); in this case the spectral characteristics are given for the proton ($^1$H) and the chemical shift of the protons relative to the proton signal of tetramethylsilane is indicated with, in brackets, the shape of the signal (s for singlet, d for doublet, t for triplet, q for quadruplet, m for multiplet, bs for broad signal) and the number of protons corresponding to the signal. By way of indication, the $^1$H NMR spectra were run at 250 MHz.

The melting points (m.p.) indicated below are generally measured using a Koffler bench and are not corrected, so they represent instantaneous melting points.

PREPARATION I 2,4-Dichloro-N-(1,1-dimethylethyl)-3-methylbenzenesulfonamide

A solution of 100 g (0.385 mol) of 2,4-dichloro-3-methylbenzenesulfonyl chloride in 1 liter of dichloromethane is prepared and 112.5 g (1.54 mol) of 1,1-dimethylethanamine are added slowly at room temperature (20–25° C.). The reaction medium is stirred for 2 hours after the addition has ended and is then hydrolyzed with water. After extraction with dichloromethane, the combined organic phases are washed with water until the pH of the washings is neutral, and are then dried over sodium sulfate and concentrated under reduced pressure. The solid residue is recrystallized from methylcyclohexane to give 80 g of the expected product in the form of a white solid (yield=70%).

M.p.=148–150° C.

PREPARATION II 2,4Dichloro-N-(1,1-dimethylethyl)-3-(bromomethyl)benzenesulfonamide 2.1 g (0.012 mol) of AIBN and 55.6 g (0.312 mol) of N-bromosuccinimide are added to a solution of 77 g (0.26 mol) of the compound obtained according to Preparation I in 1.2 liters of carbon tetrachloride. The reaction mixture is then stirred under ultraviolet irradiation and heated at the reflux point of the solvent for 4 hours. After cooling, the mixture is hydrolyzed with water and then extracted with dichloromethane. The combined organic phases are washed with water, dried over sodium sulfate and concentrated under reduced pressure. The residue is recrystallized from isopropanol to give 91 g of the expected product in the form of a white crystalline solid (yield=94%).

M.p.=157° C.

PREPARATION III 2,4-Dichloro-N-(1,1-dimethylethyl)3-[(2-methylquinolin-8-yl)oxymethyl]-benzenesulfonamide (Example 29)

A solution of 39.8 g (0.25 mol) of 2-methyl-8-hydroxyquinoline in 400 ml of dimethylformamide (DMF) is prepared and 7.5 g (0.25 mol) of an 80% suspension of sodium hydride in oil are added in small portions at room temperature. The mixture is stirred for 30 min and then cooled to 0° C. and a solution of 103.15 g (0.275 mol) of the compound obtained according to Preparation II in 120 ml of DMF is added dropwise. The mixture is subsequently stirred at room temperature for one hour and then hydrolyzed with water and extracted with dichloromethane. The organic phases are washed with water, dried over sodium sulfate and concentrated under reduced pressure to give 111.2 g of the expected product in the form of a beige pulverulent solid (yield=98%).

M.p.=191° C.

EXAMPLE 1

2,4-Dichloro-N-(1,1-dimethylethyl)-N-methyl-3-[(2-methylquinolin-8-yl)-oxymethyl]benzenesulfonamide 6.3 g (0.21 mol) of an 80% suspension of sodium hydride in oil are added in small portions at room temperature (20–25° C.) to a solution of 90.68 g (0.2 mol) of the compound obtained according to Preparation III in 650 ml of DMF. The mixture is stirred for 45 min and a solution of 31.22 g (0.22 mol) of methyl iodide in 10 ml of DMF is then added dropwise. After stirring for one hour, the reaction medium is poured into iced water. The precipitate formed is filtered off, washed with water on the filter and dried under vacuum at 70° C. to give 89.9 g of the expected product in the form of a light beige powder (yield=96%).

M.p.=160–162° C.

EXAMPLE 2

2,4-Dichloro-N-methyl-3-[(2-methylquinolin-8-yl)oxymethyl]benzenesulfonamide

A mixture of 88.8 g (0.19 mol) of the compound obtained according to Example 1 and 250 ml of 10 N hydrochloric acid is prepared and this mixture is stirred for one hour at room temperature. The reaction medium is subsequently poured into iced water and the suspended solid is then filtered off The resulting crude product is taken up with 2 N sodium hydroxide solution and extracted with dichloromethane. The organic phase is washed with water, dried over sodium sulfate and concentrated under reduced pressure to give 74.5 g of the expected product in the form of a white solid (yield=95%).

M.p.=174–176° C.

EXAMPLE 3

2,4-Dichloro-3-[(2-methylquinolin-8-yl)oxymethyl]benzenesulfonamide

A mixture of 2.26 g ($5.10^{-3}$ mol) of the compound obtained according to Preparation III and 0.59 g ($5.10^{-3}$ mol) of anisole is prepared and 20 ml of trifluoroacetic acid are then added. The solution obtained is stirred for 12 hours at room temperature and then for 5 hours at 40° C. The trifluoroacetic acid is then driven off under reduced pressure. The residue obtained is rendered neutral with 1 N sodium hydroxide solution. The product is extracted with ethyl acetate. The organic phase is washed with water, dried and then concentrated under reduced pressure. The solid obtained is purified by recrystallization from toluene to give 1.4 g of the expected product in the form of an off-white crystalline solid (yield=70%).

M.p.=206–208° C.

EXAMPLE 4

2,4-Dichloro-N-methyl-N-(phenylmethyl)-3-[(2-methylquinolin-8-yl)oxymethyl]benzenesulfonamide 60 mg ($2.10^{-3}$ mol) of a suspension of sodium hydride in oil are added to a solution of 822 mg ($2.10^{-3}$ mol) of the compound obtained according to Example 2 in 5 ml of DMF. After stirring for 30 minutes at room temperature, 376 mg ($2.2.10^{-3}$ mol) of benzyl bromide are added and the reaction mixture is stirred for one hour at 40° C. After cooling, it is poured into water and extracted with ethyl acetate. The organic phases are washed with water, dried over sodium sulfate and concentrated under reduced pressure. The solid obtained is recrystallized from ethyl acetate to give 750 mg of the expected product in the form of a white powder (yield=75%).

M.p.=154° C.

EXAMPLE 5

2,4-Dichloro-N-(1,1-dimethylethyl)-N-(phenylmethyl)-3-[(2-methylquinolin-8-yl)oxymethyl]benzenesulfonamide The expected product is obtained with a yield of 83% by following a procedure analogous to the process of Example 4, starting from the compound obtained according to Preparation III and benzyl bromide.

M.p.=167–168° C.

EXAMPLE 6

2,4-Dichloro-N-(phenylmethyl)-3-[(2-methylquinolin-8-yl)oxymethyl]benzenesulfonamide The expected product is obtained with a yield of 77% by following a procedure analogous to the process of Example 3, starting from the compound obtained according to Example 5.

M.p.=140–142° C.

EXAMPLE 7

2,4-Dichloro-N-methyl-N-[(indol-3-yl)methyl]-3-[(2-methylquinolin-8yl)oxymethyl]benzenesulfonamide The expected product is obtained in the form of a white solid with a yield of 72% by following a procedure analogous to the process of Example 1, starting from the compound obtained according to Example 2 and trimethylgramine methosulfate (N,N,N-trimethylindol-3-ylmethanaminium methanesulfonate) and purifying the crude product by chromatography on silica gel using a dichloromethane/ethyl acetate mixture (9/1, v/v) as the eluent.

M.p.=218° C.

PREPARATION IV 2,4-Dichloro-N-methyl-N-[(4-nitrophenyl)methyl]-3-[(2-methylquinolin-8-yl)-oxymethyl]benzenesulfonamide The expected product is obtained with a yield of 61% by following a procedure analogous to the process of Example 4, starting from the compound obtained according to Example 2 and 4-nitro-α-bromotoluene (i.e. 4-nitrobenzyl bromide) and recrystallizing the crude product from ethyl acetate.

M.p.=185° C.

EXAMPLE 8

2,4-Dichloro-N-methyl-N-[(4-aminophenyl)methyl]-3-[(2-methylquinolin-8-yl)oxymethyl]benzenesulfonamide dihydrochloride A solution of 0.56 g ($1.03.10^{-3}$ mol) of the compound obtained according to Preparation IV in 4 ml of methanol is prepared and 4 ml of concentrated hydrochloric acid are added, followed by 0.173 g ($3.1.10^{-3}$ mol) of iron powder. The reaction mixture is refluxed for 3 hours, with stirring, and then cooled and poured into iced water. The mixture is brought to pH 8 with 1 N sodium hydroxide solution and the precipitate formed is filtered off and then purified by chromatography on silica gel using a dichloromethane/ethyl acetate mixture (98/2, v/v) as the eluent. The solid obtained is recrystallized from a toluene/isopropyl ether mixture. The resulting compound is dissolved in ethanol and a saturated solution of hydrogen chloride in ethanol is added. The crystals formed are filtered off and dried under reduced pressure to give 0.3 g of the expected product in the form of white, slightly hygroscopic crystals (yield=50%).

M.p.=190° C.

PREPARATION V 2,4-Dichloro-N-methyl-N-[[4-[(1,1-dimethylethyl)(dimethyl)silyloxy]phenyl]methyl]-3-[(2-methylquinolin-8-yl)oxymethyl]benzenesulfonamide The expected product is obtained in the form of a creamy white solid with a yield of 78% by following a procedure analogous to the process of Example 4, starting from the compound obtained according to Example 2 and α-bromo-4-[(1,1-dimethylethyl)(dimethyl)silyloxy]toluene and purifying the crude product by chromatography on silica gel using a toluene/ethyl acetate mixture (8/2, v/v) as the eluent.

M.p.=95° C.

EXAMPLE 9

2,4-Dichloro-N-methyl-N-[(4-hydroxyphenyl)methyl]-3-[(2-methylquinolin-8-yl)oxymethyl]benzenesulfonamide 10 ml of 5 N hydrochloric acid solution are added to a suspension of 1.7 g ($2.69.10^{-3}$ mol) of the compound obtained according to Preparation V in 50 ml of methanol and the resulting mixture is then stirred for 30 minutes at room temperature. After evaporation of the methanol under reduced pressure, the residue obtained is taken up with water and the mixture is neutralized with aqueous ammonia solution. The precipitate formed is filtered off, washed with water, dried and then recrystallized from methanol to give 1.18 g of the expected product in the form of a white crystalline solid (yield=85%).

M.p.=241° C.

PREPARATION VI 2,4-Dichloro-N-methyl-N-[[3-(methoxycarbonyl)phenyl]methyl]-3-[(2-methylquinolin-8-yl)oxymethyl]benzenesulfonamide The expected product is obtained in the form of a white solid with a yield of 58% by following a procedure analogous to the process of Example 4, starting from the compound obtained according to Example 2 and methyl 3-(bromomethyl)-benzoate and purifying the crude product by chromatography on silica gel using a dichloromethane/ethyl acetate mixture (98/2, v/v) as the eluent.

M.p.=180° C.

PREPARATION VII
2,4-Dichloro-N-methyl-N-[(3carboxyphenyl)methyl]-3-[(2-methylquinolin-8-yl)oxymethyl]benzenesulfonamide 13 ml (13.10$^{-3}$ mol) of N aqueous sodium hydroxide solution are added to a suspension of 3.6 g (6.4.10$^{-3}$ mol) of the compound obtained according to Preparation VI in 50 ml of methanol. The reaction mixture is refluxed for 4 hours and then concentrated under reduced pressure. The residue is taken up with water and then acidified to pH 2 with 1 N hydrochloric acid solution. The precipitate formed is filtered off and dried to give 2.3 g of the expected product in the form of a white pulverulent solid (yield=66%).

M.p.=204° C.

EXAMPLE 10
2,4-Dichloro-N-methyl-N-[[3-(aminocarbonyl)phenyl]methyl]-3[(2-methylquinolin-8-yl)oxymethyl]benzenesulfonamide A solution of 0.5 g (0.92.10$^{-3}$ mol) of the acid obtained according to Preparation VII in 10 ml of dichloromethane and 2 ml of methanol is prepared and 0.264 g (1.38.10$^{-3}$ mol) of 1-(3-dimethylaminopropyl)-3-ethylcarbodiimide hydrochloride and 0.187 g (1.38.10$^{-3}$ mol) of 1-hydroxy-7-azabenzotriazole are added, followed by 1.5 ml of a saturated solution of ammonia in ethanol. The reaction mixture is stirred at room temperature for 20 hours. Dichloromethane is added and the organic phase is subsequently washed with sodium bicarbonate solution and then with water until the washings are neutral. The organic phase is then dried and concentrated under reduced pressure. The solid residue is recrystallized from a toluene/isopropyl ether mixture to give 0.3 g of the expected product in the form of a white solid (yield=60%).

M.p.=208° C.

EXAMPLE 11
2,4-Dichloro-N-methyl-N-[[3-(methylaminocarbonyl)phenyl]methyl]-3-[(2-methylquinolin-8-yl)oxymethyl]benzenesulfonamide The expected product is obtained in the form of a white solid with a yield of 55% by following a procedure analogous to the process of Example 10, but using a solution of methylamine in ethanol and purifying the crude product by chromatography on silica gel using a dichloromethane/ethyl acetate mixture (7/3, v/v) as the eluent, followed by recrystallization from ethyl acetate.

M.p.=195° C.

EXAMPLE 12
2,4-Dichloro-N-methyl-N-[[3-[(dimethylamino)carbonyl]phenyl]methyl]-3-[(2-methylquinolin-8-yl)oxymethyl]benzenesulfonamide The expected product is obtained in the form of a white powder with a yield of 76% by following a procedure analogous to the process of Example 10, starting from a solution of dimethylamine in ethanol and purifying the crude product by chromatography on silica gel using a dichloromethane/ethyl acetate mixture (75/25, v/v) as the eluent, followed by recrystallization from a toluene/isopropyl ether mixture.

M.p.=194° C.

EXAMPLE 13
2,4-Dichloro-N-methyl-N-[[3-[(3-hydroxypropyl)aminocarbonyl]phenyl]-methyl]-3-[(2-methylquinolin-8-yl)oxymethyl]benzenesulfonamide The expected product is obtained in the form of a white pulverulent solid with a yield of 78% by following a procedure analogous to the process of Example 10, starting from 3-aminopropanol and purifying the crude product by chromatography on silica gel using a toluene/isopropyl ether mixture as the eluent.

M.p.=98° C.

EXAMPLE 14
2,4-Dichloro-N-methyl-N-[[3-[[2-(dimethylamino)ethyl]aminocarbonyl]-phenyl]-methyl]-3-[(2-methylquinolin-8-yl)oxymethyl]benzenesulfonamide The expected product is obtained in the form of a white crystalline solid with a yield of 60% by following a procedure analogous to the process of Example 10, starting from N,N-dimethylethylenediamine and purifying the crude product by chromatography on silica gel using a dichloromethane/methanol mixture (9/1, v/v) as the eluent, followed by recrystallization from an ethyl acetate/isopropyl ether mixture.

M.p.=142° C.

EXAMPLE 15
2,4Dichloro-N-methyl-N-(2-phenylethyl)-3-[(2-methylquinolin-8-yl)oxymethyl]benzenesulfonamide The expected product is obtained with a yield of 15% by following a procedure analogous to the process of Example 4, starting from (2-iodoethyl)-benzene and purifying the crude product by chromatography on silica gel using a toluene/ethyl acetate mixture (95/5, v/v) as the eluent.

M.p.=156–160° C.

PREPARATION VIII
(7-Bromoheptyl)(1,1-dimethylethoxycarbonyl)carbamic acid 1,1-dimethylethyl ester

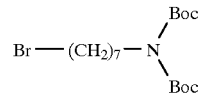

A solution of 1.15 g (5.3.10$^{-3}$ mol) of iminodicarboxylic acid bis(1,1-dimethylethyl) ester in 40 ml of DMF is prepared and 0.175 g (5.8.10$^{-3}$ mol)of an 80% suspension of sodium hydride in oil is added. After stirring for 3 hours at room temperature, 6 g (23.25.10$^{-3}$ mol) of 1,7-dibromoheptane are added and stirring is continued for 20 hours at 60° C. The reaction medium is then poured into saturated sodium chloride solution and extracted with pentane. The organic phase is washed with water, dried over sodium sulfate and concentrated under reduced pressure. The crude product is purified by chromatography on silica gel using a toluene/ethyl acetate mixture (9/1, v/v) as the eluent to give 0.43 g of the expected product in the form of a colorless oil (yield=20.7%).

$^{1}$H NMR (CDCl$_{3}$): 1.50 (m,26H); 1.85 (q, 2H); 3.40 (t, 2H); 3.55 (t, 2H).

PREPARATION IX
2,4-Dichloro-N-methyl-N-[7-[bis(1,1-dimethylethoxycarbonyl)amino]heptyl]-3-[(2-methylquinolin-8-yl)oxymethyl]benzenesulfonamide The expected product is obtained in the form of white crystals with a yield of 74% by following a procedure analogous to the process of Example 4, starting from the compound obtained according to Preparation VIII and purifying the crude product by chromatography on silica gel using a toluene/ethyl acetate mixture (9/1, v/v) as the eluent.

M.p.=96–99° C.

EXAMPLE 16
2,4-Dichloro-N-methyl-N-(7-aminoheptyl)-3-[(2-methylquinolin-8-yl)oxymethyl]benzenesulfonamide bis (trifluoroacetate)

A solution of 2.5 g ($3.45.10^{-3}$ mol) of the compound obtained according to Preparation IX in 42 ml of dichloromethane is prepared and 42 ml of trifluoroacetic acid are added slowly, the temperature being kept at about 10° C. The mixture is subsequently stirred for 45 min at room temperature (20–25° C.) and then concentrated under reduced pressure. The residue is taken up with dichloromethane and then with toluene and concentrated to dryness to give 2.57 g of the expected product in the form of beige crystals (yield=98.8%).

M.p.=66–68° C.

EXAMPLE 17
2,4-Dichloro-N-methyl-N-(6-ethoxy-6-oxohexyl)-3-[(2-methylquinolin-8-yl)-oymethyl]benzenesulfonamide The expected product is obtained with a yield of 54% by following a procedure analogous to the process of Example 4, starting from ethyl 6-bromohexanoate and purifying the crude product by recrystallization from isopropyl alcohol.

M.p.=84–86° C.

EXAMPLE 18
2,4-Dichloro-N-methyl-N-(5-carboxypentyl)-3-[(2-methylquinolin-8-yl)oxymethyl]benzenesulfonamide A solution of 1.4 g ($2.53.10^{-3}$ mol) of the compound obtained according to Example 17 in 14 ml of ethanol is heated at 40–45° C. for 3 hours in the presence of 5 ml of 1 N sodium hydroxide solution. The reaction mixture is subsequently concentrated and then taken up with water and washed with ethyl ether. The aqueous phase is acidified to pH 4 with 1 N hydrochloric acid and extracted with ethyl acetate. The resulting organic phase is washed with water, dried over sodium sulfate and concentrated under reduced pressure to give 1 g of the expected product in the form of a creamy white solid (yield=76%).

M.p.=98–102° C.

EXAMPLE 19
2,4-Dichloro-N-methyl-N-[6-(methylamino)-6-oxohexyl]-3-[(2-methylquinolin-8-yl)oxymethyl]benzenesulfonamide The expected product is obtained with a yield of 58% by following a procedure analogous to the process of Example 11, starting from the acid obtained according to Example 18 and recrystallizing the crude product from methylcyclohexane.

M.p.=110–112° C.

PREPARATION X
2,4-Dichloro-N-methyl-N-[8-[(tetrahydropyran-2-yl)oxy]octy]-3-[(2-methylquinolin-8-yl)oxymethyl]benzenesulfonamide The expected product is obtained in the form of a yellow oil with a yield of 52% by following a procedure analogous to the process of Example 4, starting from 2-(8-iodooctyl) tetrahydropyran and purifying the crude product by chromatography on silica gel using a cyclohexane/ethyl acetate mixture (8/2, v/v) as the eluent.

$^1$H NMR (CDCl$_3$): 1.20–1.90 (m, 18H); 2.74 (s, 3H); 3.08 (s, 3H); 3.22 (t, 2H); 3.37 (m, 1H); 3.50 (m, 1H); 3.72 (m, 1H); 3.86 (m, 1H); 4.56 (m, 1H); 5.67 (s, 2H); 7.23–7.50 (m, 5H); 8.02 (d, 1H); 8.07 (d, 1H).

PREPARATION XI
2,4-Dichloro-N-methyl-N-[12-[(tetrahydropyran-2-yl)oxy]dodecyl]-3-[(2methylquinolin-8-yl)oxymethyl]benzenesulfonamide The expected product is obtained in the form of a yellow oil by following a procedure analogous to the process of Preparation X, starting from 2-(12-iodododecyl) tetrahydropyran.

$^1$H NMR (CDCl$_3$): 1.10–1.90 (m, 26H); 2.74 (s, 3H); 2.86 (s, 3H); 3.22 (t, 2H); 3.37 (m, 1H); 3.48 (m, 1H); 3.75 (m, 1H); 3.88 (m, 1H); 4.57 (m, 1H); 5.67 (s, 2H); 7.23–7.50 (m, 5H); 8.03 (d, 1H); 8.08 (d, 1H).

EXAMPLE 20
2,4-Dichloro-N-methyl-N-(8-hydroxyoctyl)-3-[(2-methylquinolin-8-yl)oxymethyl]benzenesulfonamide A solution of 0.365 g ($0.58.10^{-3}$ mol) of the compound obtained according to Preparation X in 4 ml of methanol is prepared and 89 mg ($0.47.10^{-3}$ mol) of p-toluenesulfonic acid are added. The reaction mixture is stirred for 2 hours at room temperature and the methanol is then driven off under reduced pressure. The residue is taken up with water and extracted with dichloromethane and the combined organic phases are washed with water, dried over sodium sulfate and concentrated under reduced pressure. After purification by chromatography on silica gel using a cyclohexane/ethyl acetate mixture (6/4, v/v) as the eluent, 250 mg of the expected product are obtained in the form of a white solid (yield=66%).

M.p.=50° C.

EXAMPLE 21
2,4-Dichloro-N-methyl-N-(12-hydroxydodecyl)-3-[(2-methylquinolin-8-yl)oxymethyl]benzenesulfonamide The expected product is obtained in the form of a white pulverulent solid by following a procedure analogous to the process of Example 20, starting from the compound obtained according to Preparation XI.

M.p.=155° C.

PREPARATION XII
N-[4-[Bis(1,1-dimethylethoxycarbonyl)amino]butyl]-N-(1,1-dimethylethyl) -2,4dichloro-3[(2-methylquinolin-8-yl) oxymethyl]benzenesulfonamide A solution of 1.55 g ($3.42.10^{-3}$ mol) of the compound obtained according to Preparation III in 45 ml of acetonitrile is prepared and 1.41 g ($10.2.10^{-3}$ mol) of potassium carbonate and 1.50 g ($3.76.10^{-3}$ mol) of (4-iodobutyl)(1,1-dimethylethoxycarbonyl)carbamic acid 1,1-dimethylethyl ester are added. The reaction mixture is heated at the reflux point of the solvent for 25 hours, with stirring. After cooling and filtration of the mineral salts, the filtrate is concentrated to dryness. The residue is taken up with water and extracted with dichloromethane. The organic phase is washed with water until the washings are neutral, dried over sodium sulfate and concentrated under reduced pressure. The crude product is purified by chromatography on silica gel using a cyclohexane/ethyl ether mixture (3/2, v/v) as the eluent to give 0.635 g of the expected product in the form of a white solid (yield=25.6%).

M.p.=172–175° C.

EXAMPLE 22

N-(4-Aminobutyl)N-(1,1-dimethylethyl )2,4-dichloro-3-[(2-methylquinolin-8-yl)oxymethyl]benzenesulfonamide dihydrochloride A suspension of 1.21 g ($1.67.10^{-3}$ mol) of the compound obtained according to Preparation XI in 8.35 ml ($8.35.10^{-3}$ mol) of a 1 N solution of hydrogen chloride in ethyl acetate is prepared and the mixture is stirred for 15 min at room temperature. The residual precipitate is filtered off and washed on the filter with ethyl ether to give 6.58 g of the expected product in the form of a white solid (yield=58%).

M.p.=172–174° C.

EXAMPLE 23

N-(4-Aminobutyl)-N-(1,1-dimethylethyl)-2,4-dichloro-3-[(2-methylquinolin-8-yl)oxymethyl]benzenesulfonamide 5 ml of aqueous ammonia (30% solution) are added to a solution of 0.563 g ($0.94.10^{-3}$ mol) of the compound obtained according to Example 22 in 70 ml of water and the mixture is stirred for 30 min at room temperature. After extraction of the reaction medium with ethyl ether, the organic phase obtained is washed with water, dried over sodium sulfate and concentrated under reduced pressure to give 0.20 g of the expected product in the form of beige crystals (yield=40.4%).

M.p.=142–144° C.

EXAMPLE 24

N-[4-[(1-Oxoethyl)aminolbutyl]-N-(1,1-dimethylethyl)2,4-dichloro-3-[(2-methylquinolin-8-yl)oxymethyl]benzenesulfonamide 0.109 ml ($1.145.10^{-3}$ mol) of acetic anhydride is added to a solution of 0.120 g ($0.229.10^{-3}$ mol) of the compound obtained according to Example 23 in 1 ml of acetic acid and the reaction medium is stirred for 24 hours at room temperature. It is then concentrated under reduced pressure and the residue is taken up with ethyl ether to form a suspension. The precipitate obtained is filtered off and dried. 0.272 g of the expected product is thus isolated in the form of a white solid (yield=21%).

M.p.=100–102° C. (decomposition)

EXAMPLE 25

2,4-Dichloro-N-(phenylmethyl)-N-(7-hydroxyheptyl)-3-[(2-methylquinolin-8-yl]oxymethyl]benzenesulfonamide A solution of 0.5 g ($0.83.10^{-3}$ mol) of the compound obtained according to Example 6 in 10 ml of dimethylformamide is prepared and 61.5 mg ($2.10^{-3}$ mol) of an 80% suspension of sodium hydride in oil are added. After the mixture has been stirred for 30 min at room temperature, 220 mg ($1.12.10^{-3}$ mol) of 7-bromoheptanol are added. The reaction mixture is stirred for 15 hours at 40° C. and then cooled, hydrolyzed with water and extracted with ethyl acetate. The combined organic phases are washed with water until the washings are neutral, dried over sodium sulfate and concentrated under reduced pressure. After purification of the residue by chromatography on silica gel using a cyclohexane/ethyl acetate mixture (7/3, v/v) as the eluent, 150 mg of the expected product are obtained in the form of a white solid (yield=24%).

$^1$H NMR (CDCl$_3$): 0.90–1.60 (m, 10H); 2.75 (s, 3H); 3.20 (m, 2H); 3.56 (m, 2H); 4.53 (m, 2H); 5.68 (m, 2H); 7.26–7.47 (m, 10H); 8.03 (d, 1H); 8.09 (d, 1H).

EXAMPLE 26

2,4-Dichloro-N-(phenylmethyl )-N-(8-ethoxy-8-oxooctyl)-3-[(2-methylquinolin-8-yl)oxymethyl]benzenesulfonamide The expected product is obtained with a yield of 37% by following a procedure analogous to the process of Example 4, starting from the compound obtained according to Example 6 and ethyl 8-bromooctanoate and purifying the crude product by recrystallization from isopropyl alcohol.

M.p.=117° C.

EXAMPLE 27

2,4-Dichloro-N-(phenylmethyl)-N-(7-carboxyhepty l)-3-[(2-methylquinolin-8 -yl)oxymethyl]benzenesulfonamide A suspension of 1.1 g ($1.67.10^{-3}$ mol) of the compound obtained according to Example 26 in 100 ml of ethanol is prepared and a solution of 0.1 g ($2.5.10^{-3}$ mol) of sodium hydroxide in 10 ml of water is added. The reaction mixture is refluxed for 3 hours, the solvent is then evaporated off under reduced pressure and the residue is taken up with water. The resulting aqueous phase is acidified to pH 5 with 1 N hydrochloric acid. The precipitate formed is filtered off, washed with water, dried under vacuum at 60° C. and then purified by chromatography on silica gel using a dichloromethane/methanol mixture (9/1, v/v) as the eluent. After recrystallization from a toluene/isopropyl ether mixture, 0.8 g of the expected product is obtained in the form of a creamy white solid (yield=76%).

M.p.=100° C.

EXAMPLE 28

2,4-Dichloro-N-(phenylmethyl)-N-[8-(methylamino)-8-oxooctyl]-3-[(2-methylquinolin-8-yl)oxymethyl]benzenesulfonamide The expected product is obtained with a yield of 98% by following a procedure analogous to the process of Example 10, starting from the acid obtained according to Example 27 and a solution of methylamine in ethanol and purifying the crude product by chromatography on silica gel using a dichloromethane/methanol mixture (98/2, v/v) as the eluent, followed by crystallization from isopropyl ether.

M.p.=120° C.

The activity of some of the products according to the invention was evaluated in respect of their ability to bind to the bradykinin receptors. Kinins, of which bradykinin is the main representative, actually form a group of small peptides which make a substantial contribution to the inflammatory response and therefore appear to be involved in the pathophysiology of inflammatory diseases. Furthermore, bradykinin is among the most potent analgesics known. Kinins activate two types of receptor, called $B_1$ and $B_2$. The $B_2$ receptor belongs to the large family of receptors with seven transmembrane domains coupled to the G proteins. In the present invention we describe compounds which bind to the $B_2$ receptor and therefore block the binding of bradykinin.

We used the following pharmacological test: Ileum segments are isolated from male guinea-pigs of the Dunkin-Hartley strain (Iffa Credo, l'Arbresle, France) and ground in the following TES buffer: TES 25 mM, 1,10-phenanthroline 1 mM (pH 6.8), bacitracin 140 µg/ml, BSA 1 g/l. The membranes are then isolated by centrifugation (18,000 rpm; 20 min; 4° C.). The binding studies are carried out in the TES buffer using [$^3$H]-bradykinin (120 pM) and 50 µg of membrane protein per test (final volume 500 µl) with an equilibrium time of 90 min at 20° C. The percentage inhibition of the binding of [$^3$H]-bradykinin is then determined in the presence of one of the test compounds according to the invention at a concentration of $10^{-6}$ M.

The results obtained (indicated as "activity") from these tests are collated in Table I below with reference to the Examples given in the description.

The compounds of the present invention which inhibit the binding of [$^3$H]-bradykinin to the guinea-pig $B_2$ receptor (see Table I) also bind to the human $B_2$ receptor cloned and transfected in a stable manner into CHO cells (Chinese Hamster Ovary Cells). Thus, in this test, some compounds inhibit the binding of [$^3$H]bradykinin to the $B_2$ receptor by at least 95% at a concentration of 10 µW.

The compounds of the present invention can be useful in the treatment of numerous pathological conditions involving bradykinin or its homologs. These pathological conditions include septic and hemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angioedema, migraine, cerebrovascular complications, certain neurological disorders, vascular inflammatory states (for example atherosclerosis and arteritis of the lower limbs), painful states (for example toothache, menstrual pain), premature uterine contractions, cystitis and burns.

The compounds of the present invention, which can be used in the form of the free base or in the form of their non-toxic addition salts in association with a physiologically acceptable excipient, will generally be prescribed in therapy at doses of about 1 to 1000 mg/day in a form which can be administered orally, by intravenous injection, intramuscularly or subcutaneously, transdermally, by means of aerosols or by means of suppositories.

The compounds may also be administered topically, for example in the form of gels or ointments.

The compounds of the present invention are also useful as pharmacological reagents, especially for the study of hormone-receptor interactions. Use as a pharmacological reagent may require a radiolabeled derivative of one of the compounds according to the invention (for example with tritium [$^3$H] or sulfur [$^{35}$S]) in order to obtain a radioligand intended for conformational studies of the bradykinin $B_2$ receptor or for binding tests involving this type of receptor, for example for the evaluation of novel compounds which are capable of showing an affinity for the bradykinin $B_2$ receptor.

TABLE I

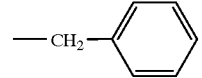

| Example no. | $R_1$ | $R_2$ | Activity % |
|---|---|---|---|
| 1 | —$CH_3$ | —$C(CH_3)_3$ | — |
| 2 | —$CH_3$ | —H | — |
| 3 | —H | —H | — |
| 4 | —$CH_3$ | 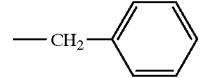 | — |
| 5 | —$C(CH_3)_3$ | 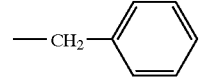 | — |
| 6 | —H | 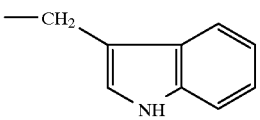 | — |
| 7 | —$CH_3$ | 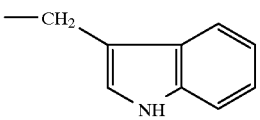 | 97.6 |

TABLE I-continued
| Example no. | $R_1$ | $R_2$ | Activity % |
|---|---|---|---|
| 8* | —CH$_3$ |  | 99.5 |
| 9 | —CH$_3$ |  | 99.5 |
| 10 | —CH$_3$ |  | 99.8 |
| 11 | —CH$_3$ |  | 100 |
| 12 | —CH$_3$ |  | 96.9 |
| 13 | —CH$_3$ |  | 99.3 |
| 14 | —CH$_3$ |  | 100 |
| 15 | —CH$_3$ | —(CH$_2$)$_2$—C$_6$H$_5$ | 97.9 |
| 16** | —CH$_3$ | —(CH$_2$)$_7$—NH$_2$ | 100 |
| 17 | —CH$_3$ | —(CH$_2$)$_5$—COOC$_2$H$_5$ | — |
| 18 | —CH$_3$ | —(CH$_2$)$_5$—COOH | — |
| 19 | —CH$_3$ | —(CH$_2$)$_5$—CONHCH$_3$ | 99.0 |
| 20 | —CH$_3$ | —(CH$_2$)$_8$—OH | 95.7 |
| 21 | —CH$_3$ | —(CH$_2$)$_{12}$—OH | 94.3 |

TABLE I-continued

[Structure: 8-(2,6-dichloro-3-sulfonamidobenzyloxy)-2-methylquinoline with R1, R2 on sulfonamide nitrogen]

| Example no. | R₁ | R₂ | Activity % |
|---|---|---|---|
| 22* | —C(CH₃)₃ | —(CH₂)₄—NH₂ | — |
| 23 | —C(CH₃)₃ | —(CH₂)₄—NH₂ | 92.8 |
| 24 | —C(CH₃)₃ | —(CH₂)₄—NH—CO—CH₃ | 90.5 |
| 25 | —CH₂—C₆H₅ | —(CH₂)₇—OH | 95.1 |
| 26 | —CH₂—C₆H₅ | —(CH₂)₇—COOC₂H₅ | — |
| 27 | —CH₂—C₆H₅ | —(CH₂)₇—COOH | — |
| 28 | —CH₂—C₆H₅ | —(CH₂)₇CONHCH₃ | 98.0 |
| 29 | —H | —C(CH₃)₃ | — |

Notes:
*dihydrochloride,
**bis(trifluoracetate)

We claim:

1. A benzenesulfonamide compound, selected from the group consisting of:

(i) the compounds of the formula

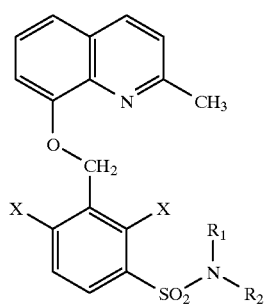

(I)

in which:

X is a halogen atom, $R_1$ and $R_2$, which are identical or different, are each a hydrogen atom or a group —A—B—$R_3$, A is a linear or branched $C_1$–$C_{12}$-alkylene chain, B is
 a single bond,
 a phenylene group of the structure

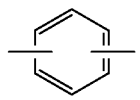

relative to which the substituents A and $R_3$ are in the ortho, meta or para position, or
 a divalent indolyl group of the structure

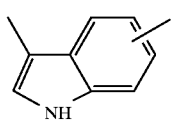

$R_3$ is —H, —OH, —NR₄R₅ or —COR₆,
$R_6$ is a group —OH, —OCH₃, —OC₂H₅ or —NR₄R₅, $R_4$ and $R_5$, which are identical or different, are each a hydrogen atom, a $C_1$–$C_4$-alkyl group with a linear or branched hydrocarbon chain, a group —$(CH_2)_n$—OH a group —$(CH_2)_n$—$N(CH_3)_2$ or a group —CO—$CH_3$, and n is an integer with a value of 2, 3 or 4; and (ii) their addition salts.

2. A compound according to claim 1, which has the formula

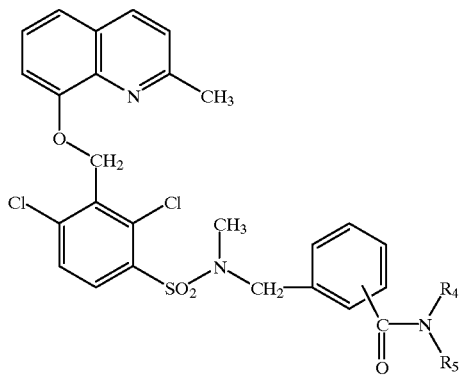

in which the amide group is in the ortho, meta or para position and $R_4$ and $R_5$, which are identical or different, are each:
a hydrogen atom,
a linear or branched $C_1$–$C_4$-alkyl group,
a group —$(CH_2)_n$—OH, or
a group —$(CH_2)_n$—$N(CH_3)_2$,
where n is an integer with a value of 2, 3 or 4; and its non-toxic acid addition salts.

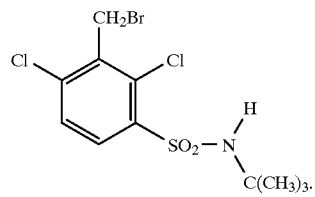

3. A method of treating pathological conditions involving bradykinin comprising administering to a patient in need thereof a bradykinin-antagonist effective amount of a benzenesulfonamide compound selected from the group consisting of the compounds of formula I according to claim 1 and their non-toxic addition salts.

4. A method for the treatment of pain comprising administering to a patient in need thereof a bradykinin-antagonist compound selected from the group consisting of compounds of formula I according to claim 1 and their non-toxic addition salts in an effective amount for the treatment of pain.

5. A method for the treatment of inflammation comprising administering to a patient in need thereof a bradykinin-antagonist compound selected from the group consisting of compounds of formula I according to claim 1 and their non-toxic addition salts in an effective amount for the treatment of inflammation.

6. A pharmaceutical composition comprising a compound according to claim 1 and a carrier or adjuvant.

7. A process for the preparation of a benzenesulfonamide compound of formula I according to claim 1 and its addition salts, comprising reacting 8-hydroxy-2-methylquinoline in the form of a phenate of the formula

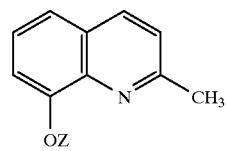

in which Z is an alkali metal atom, with a halogenated toluenesulfonamide of the formula

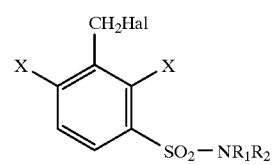

in which Hal is a halogen atom and X, $R_1$ and $R_2$ are defined as in claim 1, and wherein reactive functional groups contained in $R_1$ and/or $R_2$ are protected.

8. A process according to claim 7, which comprises the following reaction scheme:

(A) synthesizing the compound

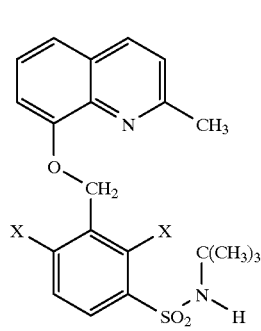

by reacting compound VIII with compound IX wherein $R_1$ is $C(CH_3)_3$;

(B) optionally, treating the compound of formula V in order to replace the amino H group with a group $R_2$ other than H as defined in claim 1 to give a compound of the formula

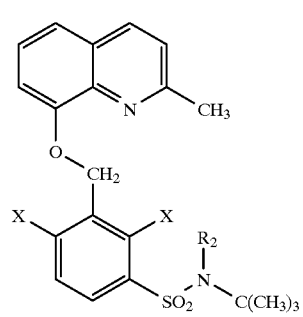

(C) optionally, treating the resulting compound of formula Va in order to replace the amino $C(CH_3)_3$ group with a hydrogen atom to give a compound of the formula

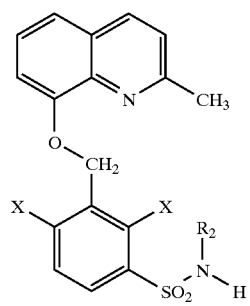

(Vb)

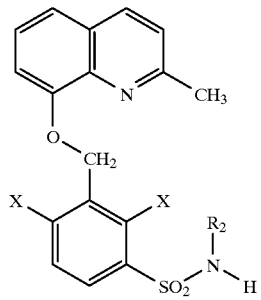

(Vb)

then (D) optionally, treating the resulting compound of formula Vb in order to replace the amino H group with a group other than H to give a compound of formula I of claim 1 in which both $R_1$ and $R_2$ are other than H, and (E) optionally reacting the free base resulting from step B, C, or D, with an acid to obtain the acid addition salt of said free base.

9. An intermediate useful for the preparation of the compounds according to claim 1, which has the formula 10. The pharmaceutical composition according to claim 6, wherein said compound is radiolabeled.

11. A method of treating pathological conditions involving bradykinin or kallidin comprising administering to a patient in need thereof an effective dose of a composition comprising a compound selected from the group consisting of at least one compound of formula I and its nontoxic addition salts as defined in claim 1.

12. A method of treating pain or inflammation comprising administering to a patient in need thereof an analgesic or anti-inflammatory effective amount of the composition of claim 6.

* * * * *